United States Patent [19]
Solar

[11] Patent Number: 5,520,647
[45] Date of Patent: May 28, 1996

[54] RAPID WITHDRAWAL CATHETER

[75] Inventor: Ronald J. Solar, San Diego, Calif.

[73] Assignee: Pameda N.V., Curacao, Netherlands

[21] Appl. No.: 87,428

[22] Filed: Jul. 2, 1993

[51] Int. Cl.⁶ .................................................. A61M 29/00
[52] U.S. Cl. ........................ 604/102; 606/194; 604/280
[58] Field of Search ............................. 604/96, 101, 160, 604/161, 280, 282, 102; 606/192, 194; 128/772

[56] References Cited

U.S. PATENT DOCUMENTS

| | | | |
|---|---|---|---|
| 4,687,469 | 8/1987 | Osypka | 604/161 |
| 4,762,129 | 8/1988 | Bonzel | 604/96 X |
| 4,983,167 | 1/1991 | Sanota | 606/194 |
| 5,141,494 | 8/1992 | Danforth et al. | 604/96 |
| 5,180,367 | 1/1993 | Kontos et al. | 604/101 |
| 5,395,332 | 3/1995 | Ressemann et al. | 604/96 |
| 5,409,458 | 4/1995 | Khairkhahan et al. | 604/96 |

Primary Examiner—Corrine M. McDermott
Attorney, Agent, or Firm—Cowan, Liebowitz & Latman

[57] ABSTRACT

This invention is directed to a balloon dilatation catheter which comprises (i) a first, inflation lumen extending therethrough and having distal and proximal ends, the distal end of said first lumen opening into and being in fluid communication with the interior of an expandable dilatation balloon having distal and proximal ends, and (ii) a second lumen extending coextensively with the first lumen and having proximal and distal portions, wherein the proximal portion of the second lumen has an opening adjacent or distal to the proximal end of the first lumen, the distal section of the second lumen is exterior to the balloon, the distal end of the second lumen is open, and the second lumen is capable of receiving a guidewire in a sliding fit. The proximal end of the guidewire may have a removedly mounted slitter, and optionally there may be a hub means in fluid communication with the distal end of the second lumen.

4 Claims, 4 Drawing Sheets

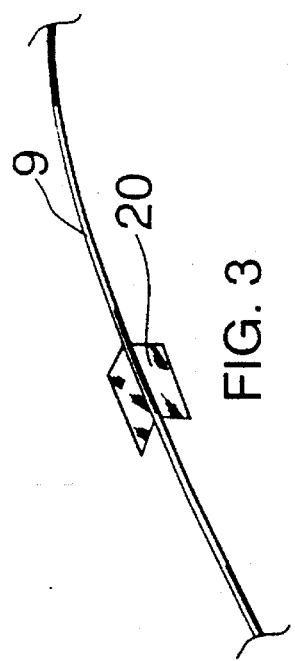
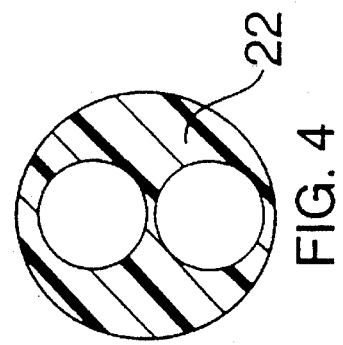
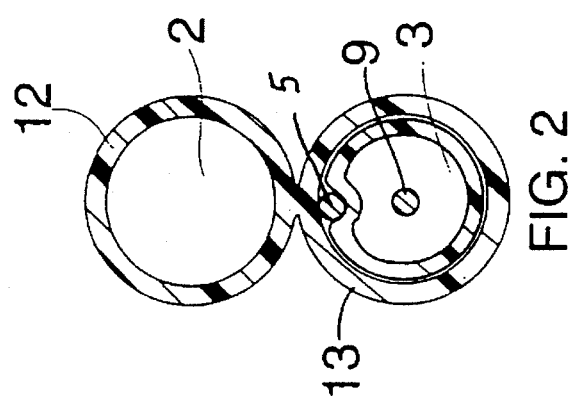
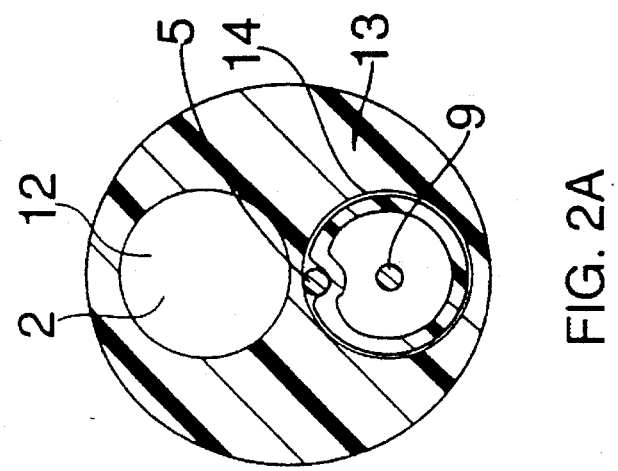

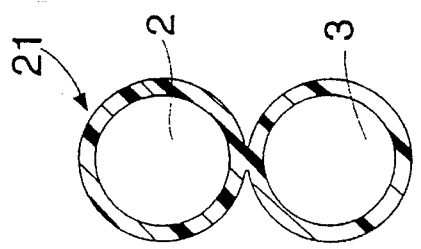
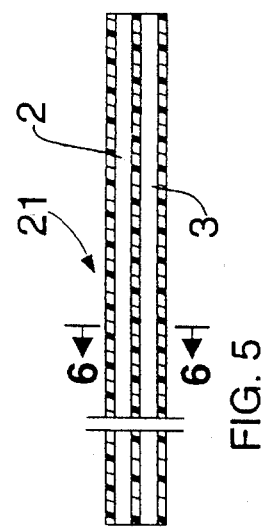
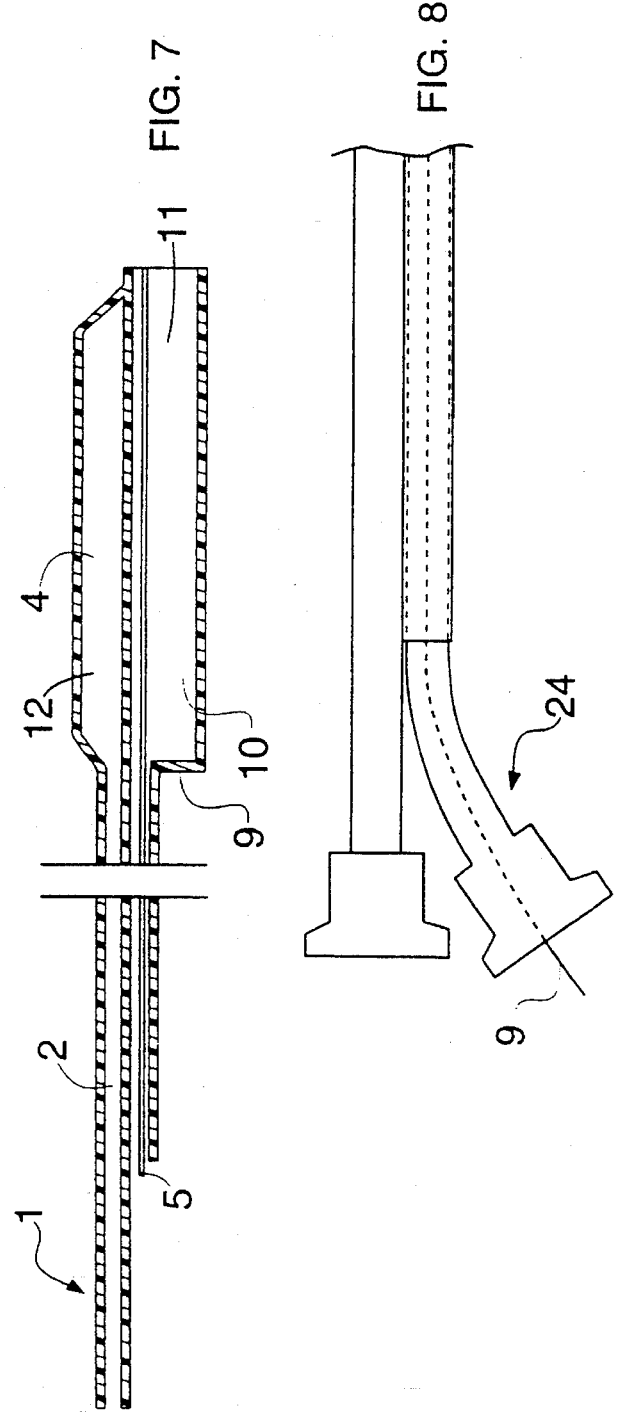

RAPID WITHDRAWAL CATHETER

FIELD OF THE INVENTION

This invention is directed to an angioplasty apparatus for facilitating rapid withdrawal of a balloon catheter. More particularly, this invention is directed to a rapid withdrawal catheter system whereby a double-lumen dilatation balloon catheter has an opening in one lumen adjacent its proximal end for a guidewire and means to separate the guidewire from the lumen.

BACKGROUND OF THE INVENTION

During angioplasty procedures it is often necessary to remove the dilatation catheter and leave the guidewire across the stenotic segment. This is required, for example, to exchange one dilatation catheter for another dilatation catheter or other therapeutic or diagnostic device. To do so requires manipulation of lengthy exchange wires, which is time-consuming and awkward to the extent that two operators are required. A current approach to dealing with this is the "monorail" system wherein a dilatation catheter has a structure such that only the distal portion of the catheter tracks a guidewire. Examples of such systems are described in Yock, U.S. Pat. Nos. 5,040,548 and 5,061,273, Bonzel, U.S. Pat. No. 4,762,129, and Kramer, U.S. Pat. No. 5,135,535, all of which are incorporated herein by reference.

In the known monorail systems the pushing force on the dilatation catheter is eccentric to the guidewire, such that there is not total responsiveness in the system as the operator attempts to manipulate the dilatation catheter along the guidewire. This can cause binding and failure to move the catheter through tortuous arterial segments and tight stenoses. In these circumstances an over-the-wire design, wherein the guidewire is within a lumen of the length of the catheter, provides superior tracking and transmission of axial force to cross tight stenoses. Thus, there is a need for an over-the-wire type catheter that can be rapidly and easily removed from the guidewire, without need to exchange the guidewire. Furthermore, it is advantageous to use as a subsequent catheter a monorail system such as is described in commonly assigned, co-pending U.S. patent application Ser. No. 07/969,887, filed Oct. 30, 1992, wherein there is co-linear design between a pushing wire and the guidewire and thus more positive tracking.

OBJECTS OF THE INVENTION

It is an object of the invention to provide a balloon dilatation system capable of having improved tracking characteristics and capable of rapid withdrawal.

It is also an object of the invention to provide a double lumen dilatation catheter wherein the guidewire lumen is positioned exterior to the dilatation balloon.

It is a further object of the invention to provide a rapid withdrawal balloon dilatation catheter that is simple to manufacture.

These and other objects of the invention will become more apparent from the description below.

BRIEF DESCRIPTION OF THE DRAWINGS

FIG. 2 represents a cross-sectional view along the line 2—2; in FIG. 1

FIG. 2A represents a cross-sectional view similar to that of FIG. 2 of an alternative embodiment of the invention;

FIG. 3 represents an embodiment of the invention wherein the distal portion of the guidewire comprises a splitting means;

FIG. 4 represents a cross-sectional view of extruded tubing from which the catheter of the invention can be formed;

FIGS. 5 and 7 each represents a cross-sectional view of the distal portion of the catheter of the invention as it is being formed;

FIG. 6 represents a cross-sectional view along the line 6—6 of the workpiece in FIG. 5; and FIG. 8 represents an embodiment of the invention with a hub at the proximal opening of the guidewire lumen.

DETAILED DESCRIPTION OF THE INVENTION

According to the invention, a balloon dilatation catheter comprises two substantially longitudinal coextensive lumens wherein the distal portion of one lumen terminates in a dilatation balloon. The other, second lumen is open at its proximal and distal ends to provide a passageway for a guidewire that extends distally through the open distal end of the second lumen. Moreover, the second lumen optionally comprises a pushing wire that extends from the proximal portion of the catheter to a point adjacent or proximal to the distal end of the catheter.

Figure 1:
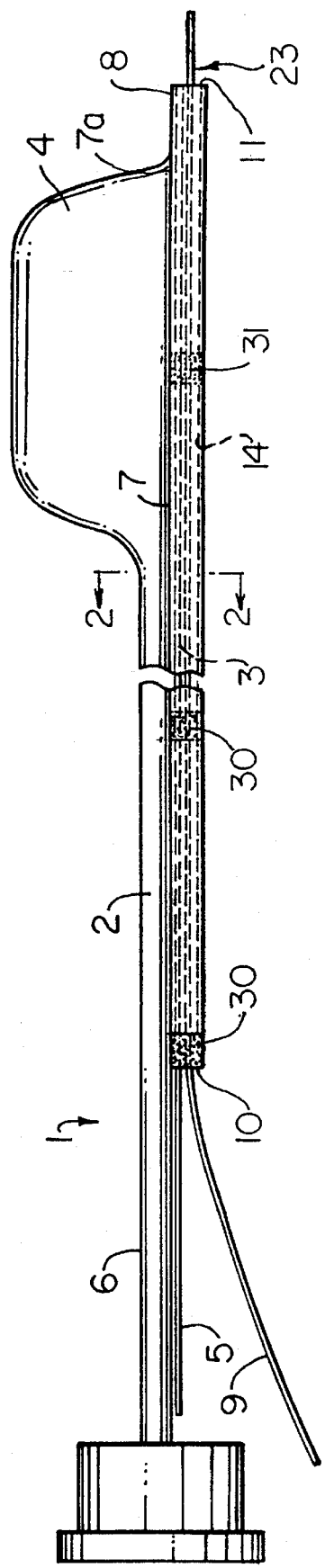
FIG. 1 and 1A each depict a cross-sectional view of a balloon dilatation catheter system according to the invention.

The invention can perhaps be better appreciated by making reference to the drawings. FIG. 1 depicts a cross-sectional view of a balloon dilatation catheter 1 having substantially coextensively extending inflation lumen 2 and guidewire lumen 3. Lumen 2 terminates in a dilatation balloon 4 which is inflated and deflated through lumen 2.

Figure 1A:
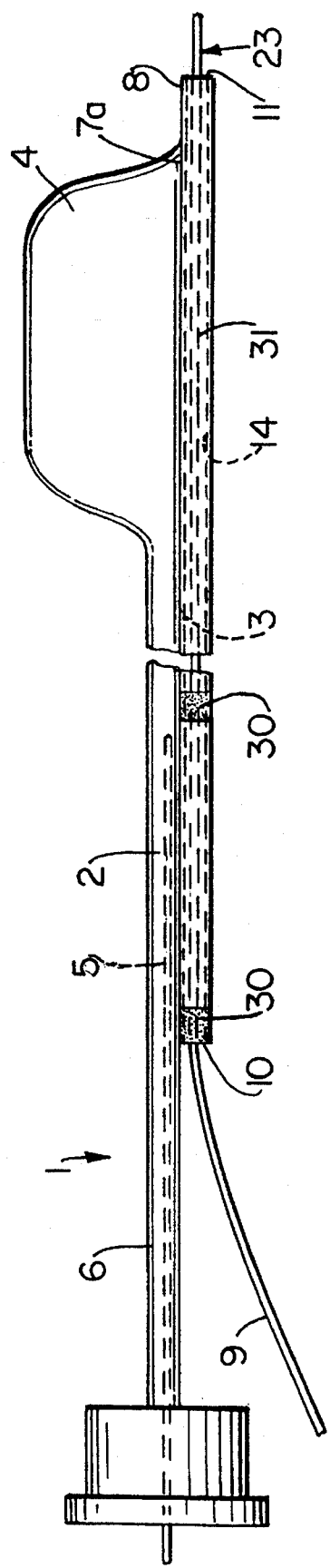

Lumen 3 optionally contains a stiffening or pushing wire 5, which extends from the proximal end of catheter 1 to a position 7 proximal or adjacent to balloon 4 or optionally to position 7a adjacent to the distal end of the catheter. The pushing wire 5 is secured along its length by suitable means, such as adhesive or heat fixation to the interior surface 8 of lumen 3. Also, the distal portion of pushing wire 5 is preferably tapered distally to provide a smooth transition in axial stiffness. The pushing wire 5 will become less stiff as the diameter of pushing wire 5 narrows in the distal direction. The tapering is substantially linear over the distal 1 to 30 cm of the pushing wire 5. Pushing wire 5 may optionally be located in the inflation lumen 2 as shown in FIG. 1A.

The distal portion of a guidewire 9 is threaded through opening 10 into the proximal end of lumen 3. As the guide-wire 9 is threaded through lumen 3, it exits through distal opening 11.

FIG. 2 represents a cross-sectional view in the distal direction showing how lumens 2 and 3 relate to one another and how pushing wire 5 can be positioned within lumen 3. Lumen walls 12 and 13 can each have a thickness of from about 0.5 to 3 mil and may be of different thicknesses. FIG. 2a represents an alternative embodiment wherein the external aspect of the catheter is more rounded.

The lumen walls 12 and 13 are comprised of materials conventional to balloon dilatation catheters. Suitable materials include polyolefins such as polyethylene, polyethylene terepthalate, urethane, polyester, and various copolymers thereof. Pushing wire 5 can be made from any rigid, medically acceptable material suitable for such use, including, but not limited to wires or hypotubes comprised of stainless steel or other rigid materials.

The construction according to the invention leads to flexibility in product design. For example, the choice of pushing wire or its absence allows the designer to impart various features to the catheter in the form of various flexibility and pushability combinations. Also, a hollow pushing wire would facilitate infusion of fluids, drugs, and/or contrast media through the catheter into the distal vasculature. Further, it is within the scope of the invention that catheter 1 may have a third coextensive lumen that would similarly facilitate infusion of liquids, drugs and/or contrast media or even provide an alternative location for pushing wire 5.

In a preferred embodiment of the invention, as shown in FIG. 1, a lubricious coating or a section of thin tubing 14 of lubricious material is sealed into lumen 3. There are several known materials suitable for this purpose, such as polytetrafluoroethylene (available as TEFLON® from dupont), polysiloxanes, etc. In this embodiment the tubing section 14 can hold the pushing wire 5 in position.

According to a preferred aspect of the invention shown in FIG. 3, a slitting means 20 is removedly mounted proximally on guidewire 9. Then, as the catheter 1 is withdrawn with guidewire 9 remaining in position, for example, with its distal end across a stenotic lesion, lumen 3 engages the slitter means 20, lumen 3 is slit, and catheter 1 is separated from guidewire 9. This would eliminate the requirement for the operator to change hands as catheter 1 is removed and would facilitate quick removal of the catheter 1 from the patient. In addition, since the balloon is not slit, it can be reinflated outside the patient to verify the inflated diameter.

The catheter 1 may have visual length markings 30 along its shaft that would enable the operator to predict when the catheter 1 would exit the guiding catheter into the vasculature. This would reduce the fluoroscope time. The preferred design would put the markings directly on pushing wire 5 (heat shrink tubing rings, inks, paints, etc.). Since pushing wire 5 is substantially positioned within the guidewire lumen 3, the markings would not be exposed to the patient (i.e., markings would not come off, and materials which could be toxic if exposed may be used). If a thin tubing 14 is used within lumen 3, the markings could alternately be placed within or, preferably, around tubing 14.

The preparation of a catheter 1 according to the invention is shown in FIGS. 4, 5, 6 and 7. Double lumen workpiece 21 can be prepared by methods well known to those skilled in the art. In a preferred method workpiece 21 is prepared by sealingly clamping the distal end of double lumen extruded tubing 22, a cross-section of which is shown in FIG. 4, and applying heat and pressure to blow the extruded tubing 22 to form workpiece 21.

After workpiece 21 is prepared, additional heat and pressure are applied to cause the proximal portion of lumen 2 to shrink, leaving the distal portion of lumen 2 to form the balloon 4. Heat sealing or application of suitable adhesive seals the distal portion of balloon 4.

Lubricious tubing 14 is inserted into lumen 3. Heat is applied to cause lumen 3 to shrink such that lubricous tubing 14 is positively engaged within lumen 3. Optionally, pushing wire 5 is inserted into lumen 3 prior to shrinking between tubing 14 and lumen wall 13. When lumen 3 shrinks, pushing wire 5 and lubricous tubing 14 are fixedly constrained within lumen 3.

In another embodiment of the invention, a removable hub means 24 is in fluid communication with the proximal opening 10 of lumen 3, as shown in FIG. 8. Such hub means 24 facilitates infusion of fluids or drugs through lumen 3. Optionally, hub means 24 may extend distally into lumen 3 along guidewire 9. Also, if tubing 14 were to extend proximally from opening 10, hub means 24 may be adjoined to and in fluid communication with tubing 14.

Hub means 24 is removely bonded, joined, or attached to either proximal opening 10 or tubing 14. Therefore, when hub means 24 is to be removed, such as when catheter 1 is to be removed, removal of hub means 24 is accomplished by pulling hub means 24 in the proximal direction over the proximal end of guidewire 9.

An advantage of the design and preparation according to the invention is that the catheter can be of integral design and multiple bonding steps can be avoided. The balloon and both lumens can be formed from a single piece. This design permits improvements in manufacturing yields, quality, and reliability due to simplified construction.

Guidewire 9 may be a conventional guidewire, preferably a spring guidewire, as is well known. Typical guidewires are shown in U.S. Pat. Nos. 4,757,827, 4,815,478, 4,813,434, 4,619,274, 4,554,929, 4,545,390, 4,538,622, 3,906,938, 3,973,556, and 4,719,924, all of which are incorporated herein by reference. In addition, the shaft of guidewire 9 could be solid or hollow, such as a hypotube, with an open distal end, to facilitate drug infusion.

Operation and use of the angioplasty apparatus shown in FIG. 1 may now be briefly described as follows: A guiding catheter is inserted into the coronary artery in a conventional manner. The guidewire 9 is then introduced into the balloon dilatation catheter 1 by either a back loading technique where the proximal extremity of the guidewire 9 is inserted backwardly through opening 11 of balloon dilatation catheter 1, or a forward loading technique, where the distal extremity of the guidewire 9 is inserted in proximal opening 10. The guidewire 9 is advanced proximally until the proximal extremity of the guidewire is near the proximal extremity of the dilatation catheter 1 and so that the distal extremity of the guidewire 9 with its flexible or floppy tip 23 protrudes at least partially from the distal extremity of the balloon dilatation catheter.

A guidewire gripping means, or torquer, such as a slitter 20, is now attached to the guidewire 9 near its proximal extremity, and the guidewire 9 is then advanced ahead of the balloon dilatation catheter 1 until it enters the arterial vessel of the patient. The balloon dilatation catheter 1 is held stable by the fingers of the hand while the guidewire 9 is being advanced. The positioning of the guidewire 9 in the desired arterial vessel can be observed under a fluoroscope by using x-ray or fluoroscopic techniques well known to those skilled in the art. The torquer can be utilized to rotate the guidewire 9 to facilitate positioning of its distal tip in the desired arterial vessel so that the distal extremity of the guidewire can be advanced into the stenosis which it is desired to open or enlarge.

As soon as the guidewire 9 is in the desired location, it can be held stationary by two fingers of the hand and then the balloon dilatation catheter 1 is advanced over the guidewire until the deflated balloon 4 is across the desired lesion or stenosis. If any difficulty is encountered by the person conducting the procedure in introducing the balloon dilatation catheter so that the balloon 4 resists crossing the lesions or stenosis, the guidewire 9 can be retracted slightly. The operator then can observe under the fluoroscope to see that the tip of the guidewire 9 is wiggling in the bloodstream indicating that it is free to move in the bloodstream. Then the operator can grasp both the guidewire and the dilatation catheter in one hand and advance them as a unit so that they can cross the stenosis as a unit. It has been found by utilizing such a procedure, greater pushability can be obtained in advancing the balloon dilatation catheter across the stenosis. In other words, more force can be applied to the balloon to cause it to cross the stenosis or lesion in case the opening there is very small.

When the balloon 4 has crossed the stenosis or lesion, the balloon 4 can be inflated in a conventional manner by introducing a radiopaque contrast liquid through the lumen 2. After the inflation has occurred and the desired operation has been performed by enlarging the opening in the stenosis, the balloon dilatation catheter 1 can be removed very rapidly by holding the slitting means 20 stationary and pulling back catheter 1 such that the guidewire lumen 3 is slit and the catheter is separated from the guidewire. As soon as the balloon dilatation catheter 1 has been removed from the guiding catheter, another injection of radiographic contrast liquid can be introduced through the guiding catheter to observe whether or not the balloon dilatation procedure which has been performed on the lesion or stenosis to the satisfaction of the person performing the procedure. With the guidewire still in place, access to the lesion is maintained.

If it is ascertained by the operator that additional therapy or diagnostics relating to the stenosis is desired, this can be accomplished very rapidly by selecting the desired catheter of a monorail type, preferably of the type described in co-pending U.S. patent application Ser. No. 07/969,887, filed Oct. 30, 1992, and advancing it over the guidewire. The procedural steps described above can be repeated as necessary.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A method for removing a balloon from a blood vessel dilatation catheter of a balloon dilatation catheter system, wherein the balloon dilatation catheter system comprises:

a catheter shaft which defines a first inflation lumen and a second lumen, said catheter shaft having proximal and distal portions, an inflatable dilatation balloon sealingly connected to said catheter shaft, a pushing wire that extends within said catheter shaft, and a guidewire, wherein the first lumen extends through the length of said catheter shaft and has distal and proximal ends, said distal end opening into and being in fluid communication with the interior of said inflatable dilatation balloon, and wherein the second lumen extends coextensively with said first lumen and has proximal and distal portions, said proximal portion of said second lumen having an opening distal to the proximal end of said first lumen, said distal section of said second lumen being exterior to said inflatable dilatation balloon, said distal end of said second lumen being open, and said second lumen receiving the guidewire in a sliding fit, said method comprising the steps of:

(a) attaching a slitting means to the guidewire, wherein said catheter extends distally into a patient's blood vessel;

(b) causing the guidewire to remain stationary; and (c) pulling the balloon dilatation catheter in the proximal direction to cause the lumen in which the guidewire is contained to open, thus permitting removal of the balloon dilatation catheter while leaving the guidewire in place.

2. A method for removing from a blood vessel a balloon dilatation catheter of a balloon dilatation catheter system, wherein the balloon dilatation catheter system comprises:

a catheter shaft which defines a first inflation lumen and a second lumen, said catheter shaft having proximal and distal portions, an inflatable dilatation balloon sealingly connected to said catheter shaft, a pushing wire that extends within said catheter shaft, and a guidewire, wherein the first lumen extends through the length of said catheter shaft and has distal and proximal ends, said distal end opening into and being in fluid communication with the interior of said inflatable dilatation balloon, and wherein the second lumen extends coextensively with said first lumen and has proximal and distal portions, said proximal portion of said second lumen having an opening distal to the proximal end of said first lumen, said distal section of said second lumen being exterior to said inflatable dilatation balloon, said distal end of said second lumen being open, said second lumen receiving the guidewire in a sliding fit, said second lumen having a removable hub at the proximal end of the second lumen in fluid communication with the second lumen, said method comprising the steps of:

(a) removing the removable hub attached to the second lumen of the balloon dilatation catheter, wherein said catheter system extends distally into a patient's blood vessel;

(b) attaching a slitting means to the guidewire;

(c) causing the guidewire to remain stationary; and (d) pulling the balloon dilatation catheter in the proximal direction to cause the lumen in which the guidewire is contained to open, thus permitting removal of the balloon dilatation catheter while leaving the guidewire in place.

3. A balloon dilatation catheter which comprises a catheter shaft which defines a first inflation lumen and a second lumen, said catheter shaft having proximal and distal portions, and an inflatable dilatation balloon sealingly connected to said catheter shaft, wherein the first lumen extends through the length of said catheter shaft and has distal and proximal ends, said distal end opening into and being in fluid communication with the interior of said inflatable dilatation balloon, and wherein the second lumen extends coextensively with said first lumen and has proximal and distal portions and an inner wall, said proximal portion of said second lumen having an opening distal to the proximal end of said first lumen, said distal section of said second lumen being exterior to said inflatable dilatation balloon, said distal end of said second lumen being open, said second lumen comprising a pushing wire and lubricious material in the form of concentrically positioned tubing and said pushing wire being held in position in a pressure fit between said lubricious tubing and the inner wall of said second lumen, and said second lumen being capable of receiving a guidewire in a sliding fit.

4. A balloon dilatation catheter which comprises a catheter shaft which defines a first inflation lumen and a second lumen, said catheter shaft having proximal and distal portions, and an inflatable dilatation balloon sealingly connected to said catheter shaft, wherein the first lumen extends thought the length of said catheter shaft and has distal and proximal ends, said distal end opening into and being in fluid communication with the interior of said inflatable dilatation balloon, and wherein the second lumen extends coextensively with said first lumen and has proximal and distal portions and an inner wall, said proximal portion of said second lumen having an opening adjacent to the proximal end of said first lumen, said distal section of said second lumen being exterior to said inflatable dilatation balloon, said distal end of said second lumem being open, said second lumen comprising a pushing wire and lubricious material in the form of concentrically positioned tubing and said pushing wire being held in position in a pressure fit between said lubricious tubing and the inner wall of said second lumen, and said second lumen being capable of receiving a guidewire in a sliding fit.

\* \* \* \* \*